United States Patent [19]

Asato et al.

[11] Patent Number: 4,649,158
[45] Date of Patent: Mar. 10, 1987

[54] NOVEL SALTS OF 1-(AMINODIHALOPHENYL)-2-AMINOETHANOLS AND ANTILIPOGENIC COMPOSITIONS PREPARED THEREFROM

[75] Inventors: Goro Asato, Titusville; Lawrence J. Ross, Martinsville, both of N.J.

[73] Assignee: American Cyanamid Company, Stamford, Conn.

[21] Appl. No.: 785,621

[22] Filed: Oct. 7, 1985

Related U.S. Application Data

[62] Division of Ser. No. 462,746, Feb. 1, 1983, Pat. No. 4,552,897.

[51] Int. Cl.$^4$ .......................................... A61K 31/205
[52] U.S. Cl. ...................................... 514/554; 514/653
[58] Field of Search ................................ 514/653, 554

[56] References Cited

U.S. PATENT DOCUMENTS

| | | | |
|---|---|---|---|
| 3,536,712 | 10/1970 | Keck et al. | 564/363 |
| 4,170,487 | 10/1979 | Robertson et al. | 106/288 Q X |
| 4,177,082 | 12/1979 | Robertson | 106/288 Q X |
| 4,404,224 | 9/1983 | Asato | 564/99 X |

FOREIGN PATENT DOCUMENTS 26298  4/1981  European Pat. Off. .

Primary Examiner—Frederick E. Waddell
Attorney, Agent, or Firm—Alice C. Brennan

[57] ABSTRACT

Novel acid addition salts of 1-(aminodihalophenyl)-2-aminoethanols and method of preparation thereof. The invention describes certain non-dusting, antilipogenic compositions used as animal feed supplements and/or concentrates and a method for increasing weight gain and improving the lean meat to fat ratio of warm-blooded animals.

1 Claim, No Drawings

NOVEL SALTS OF 1-(AMINODIHALOPHENYL)-2-AMINOETHANOLS AND ANTILIPOGENIC COMPOSITIONS PREPARED THEREFROM

This application is a division of Ser. No. 462,746, filed Feb. 1, 1983 now U.S. Pat. No. 4,552,897, issued on Nov. 12, 1985.

The invention herein described relates to novel acid addition salts of and method of preparation thereof of biologically active 1-(aminodihalophenyl)-2-aminoethanols of structural formula (I)

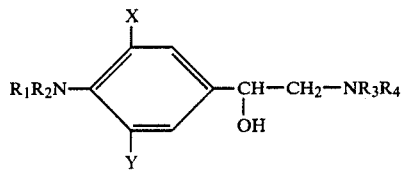
(I)

wherein $R_1$ is hydrogen or $C_1$–$C_{14}$ alkyl; $R_2$ is hydrogen or methyl, provided that when $R_1$ is $C_2$–$C_{14}$ alkyl, then $R_2$ is hydrogen; $R_3$ and $R_4$ each is hydrogen or $C_1$–$C_6$ alkyl; X and Y each is bromine, chlorine, fluorine or iodine. The acids used in the preparation of said salts of the compounds of formula (I) are carboxylic acids selected from oleic acid, linoleic acid, linolenic acid, tall oil fatty acids, and abietic acid, and mixtures thereof.

The invention also relates to certain non-dusting antilipogenic formulations prepared from the above described salts of the compounds of formula (I), and to a method for increasing weight gain and improving the lean meat to fat ratio of warm-blooded meat animals.

By way of background, certain related 1-(aminodihalophenyl)-2-aminoethanols, substitution products thereof, and acid addition salts thereof are disclosed in U.S. Pat. No. 3,536,712. This patent discloses methods for the preparation of said compounds and their uses for enhancing blood circulation, as bronchodilators, analgesics, sedatives, antipyretics and the like in warm-blooded animals. Other related 1-(aminodihalophenyl)-2-aminoethanols and their derivatives are disclosed in Japanese Kokai No. 77 83,619 (C.A. 87, 201061r), German Offenlegungsschrift No. 2,804,625 (1979), German Offenlegungsschrift No. 2,157,040 (1973), German Offlegungsschrift No. 2,261,914 (1974), European Patent Application No. 8,715 (1980), and Netherlands Patent Application No. 7,303,612 (1973). These applications disclose uses of these compounds as analgesics; broncholytic, antiinflammatory, uterine spasmolytic, β-mimetic and/or β-blocking activities; mobilizing body fat; and treating allergies among other uses.

Compounds of formula (I), analogs and salts thereof, generally have a profound and adverse effect on the normal activity of the human heart when introduced into the circulatory system via inhalation, ingestion and/or transdermal absorption as from a contaminated environment. These compounds are usually isolated and used as the free bases, and/or salts thereof, prepared with acids such as hydrochloric acid, phosphoric acid, acetic acid, citric acid and the like. The bases and some of the salts are friable and thus may form dusts, which in turn may contaminate the environment creating a distinct hazard to all those who have to be present in, or have to traverse said environment.

The cost of raising meat animals has increased markedly in recent years due to energy costs, market fluctuations and other factors. The necessity of providing adequate meat protein supplies to a constantly expanding population remains a challenge to animal husbandry. A mechanism for increasing the quantity of animal protein supplies while maintaining ordinary feed requirements would facilitate delivery of required food supplies.

In light of the foregoing summary of some demands and limitations of conventional methods for the production of meat products, an improved method for quantitative and/or qualitative improvement in animal crop yields is highly desirable. Objects of this invention are: to provide new and useful compounds, compositions; methods of preparation thereof; methods of use thereof; and also to provide methods which will eliminate hazards associated with dusting in the course of the manufacture and/or formulation of compounds of formula (I). These objects are manifest in the following description and particularly delineated in the appended claims.

Advantageously, the novel acid salts of the present invention exhibit improved solubility in a number of pharmaceutically acceptable solvents approved for use in animal feeds. Further, the novel salts of this invention may be prepared directly in the medium in which formula (I) compounds are formed without separation of said formula (I) free base. Then the solvent may be displaced by the selected pharmaceutically acceptable solvent and resulting salt solution utilized in the preparation of animal feeds and/or animal feed supplements; thus, avoiding handling or exposure of any solid capable of dusting.

These novel salts of 1-(aminodihalophenyl)-2-aminoethanols may be graphically illustrated by formula (II)

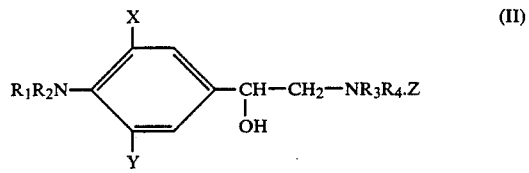
(II)

wherein $R_1$ is hydrogen or $C_1$–$C_{14}$ alkyl; $R_2$ is hydrogen or methyl; provided that when $R_1$ is $C_2$–$C_{14}$ alkyl then $R_2$ is hydrogen; $R_3$ and $R_4$ are hydrogen or $C_1$–$C_6$ alkyl; X and Y are bromine, chlorine, fluorine or iodine; Z is a carboxylic acid selected from oleic acid, linoleic acid, linolenic acid, tall oil fatty acids, abietic acid and mixtures thereof.

European Patent Application, No. EP-26-298 (4/8/81) discloses a method for the depression of fat deposition in warm-blooded animals, particularly farm and domestic animals, such as swine, sheep, goats, cattle, rabbits, poultry, dogs and cats by administering an effective amount of certain 1-(aminodihalophenyl)-2-aminoethanes, substitution products thereof or certain acid addition salts thereof in said animals feed. An especially preferred compound of said application is 1-(4'-amino-3',5'-dichlorophenyl)-t-butylaminoethanol and salts thereof with hydrochloric, phosphoric, acetic, propionic, citric and gluconic acids. These friable bases and salts may form dusts during their manufacture or during the preparation of conventional dry formulations therefrom, and thus contaminate the immediate environment.

The novel salts of the invention as represented and defined by formula (II) above, are eminently suitable for the preparation of non-dusting antilipogenic formulations. A more preferred group of compounds of formula (II) are those salts wherein the acid is selected from abietic acid, tall oil fatty acids, oleic acid, linoleic acid, linolenic acid and mixtures thereof; $R_1$, $R_2$ and $R_3$ are hydrogen; X and Y are both chlorine. An especially preferred salt is 1-(4'-amino-3',5'-dichlorophenyl)-2-t-butylaminoethanol oleate.

The above discussed formula (II) salts of the invention may be conveniently prepared by adjusting the pH of the reaction mixture to a range of pH 7-11 in which a compound of formula (I) was prepared, to a value that said compound is present as the free base, followed by the addition of 1.0 to 1.5 molar equivalent of a carboxylic acid, as defined under "Z", and allowing a sufficient amount of time to elapse until the formulation of the appropriate formula (II) salt is essentially complete. Alternatively, these novel salts of the invention may be conveniently and easily prepared by dissolving the appropriate 1-(aminodihalophenyl)-2-aminoethanol in an inert solvent such as methylene dichloride, chloroform, acetone, methanol and mixtures thereof, adding the appropriate amount (1.0 to 1.5 molar equivalent) of acid selected, and maintaining the thus obtained reaction mixture at a temperature range from about 15° C. to about the boiling point of the selected solvent at atmospheric pressure, for a period of time sufficient to essentially complete the salt forming reaction. This time period may range from a few minutes to several hours. The thus obtained salts of formula (II) may be recovered from the reaction mixture by standard laboratory methods known in the art.

As previously stated the formula (II) salts of the invention are eminently suitable for the preparation of animal feed compositions, premixes and/or additives without the threat of contaminating the immediate environment with same. An added advantage of these salts is that they are selectively soluble in one or more pharmaceutically acceptable solvents such as propylene glycol, coconut fatty acid methyl ester (an approximately 50:50 mixture of methyl palmitate and methyl oleate), mineral oil-sorbitan monooleate mixtures, corn oil, soybean oil and mixtures thereof; preferably propylene glycol, coconut fatty acid methyl ester and mixtures of mineral oil with sorbitan monooleate.

Animal feed compositions effective for increasing lean meat deposition and for improving lean meat to fat ratio in poultry, swine, sheep, goats, cattle and domestic pets are generally prepared by admixing on a weight basis about 1 to 15% of a formula (II) salt with about 85 to 99% of a solvent or mixture of solvents selected from the group named above. The mixture is then agitated and heated if necessary until a clear solution forms. Alternatively, such a solution may be prepared by admixing about 1 to 15% by weight of an "aminoalcohol" of the appropriate formula with an equimolar or excess amount of the carboxylic acid selected; totaling said mixture to 100% with the solvent or solvent mixture selected; and then agitating (and heating if necessary) said mixture until a clear solution occurs. The thus prepared solution(s) may be sprayed on and/or admixed with a sufficient amount of animal feed to provide about 1 to 1000 ppm of said compound in the feed.

The above solutions may also be used for the preparation of animal feed supplements by admixing on a weight basis about 5 to 35% of said solution with about 65 to 95% by weight of a suitable carrier or diluent. Carriers or diluents suitable for use to make up the feed supplement compositions include the following: alfalfa meal, soybean meal, cottonseed oil meal, linseed oil meal, cornmeal, urea, bone meal, corncob meal, corncob grits and the like. The carrier/diluent promotes a uniform distribution of the active ingredients in the finished feed into which the supplement is blended. It thus performs an important function by ensuring proper distribution of the active ingredient throughout the feed.

If the supplement is used as a top dressing for feed, it likewise helps to ensure uniformity of distribution of the active material across the top of the dressed feed.

The preferred medicated swine, cattle, sheep and goat feeds generally contain about 0.01 to 400 grams of active ingredient per ton of feed, with the optimum amount usually being about 0.05 to 10 grams per ton of feed. The preferred poultry and domestic pet feeds usually contain about 0.01 to 400 grams (preferably 0.125 to 10 grams) of active ingredient per ton of feed.

In a preferred embodiment of the invention, on a weight basis, about 5 to 10% of 1-(4-amino-3',5'-dichlorophenyl)-2-t-butylaminoethanol, about 5 to 10% of oleic acid, about 2 to 25% and (preferably 2 to 10%) of sorbitan monooleate, and mineral oil used in sufficient quantities to total the composition to 100%, are mixed and agitated until a clear solution forms. Next on a weight basis, about 3 to 10% of said solution is mixed with about 90 to 97% of 40–60 mesh corncob grits, and the mixture is stirred until the solution is absorbed.

In yet another preferred embodiment, on a weight basis, about 0.1 to 0.5% of 1-(4'-amino-3',5=-dichlorophenyl)-2-t-butylaminoethanol, about 0.11 to 0.55% of tall oil fatty acid and 4.79 to 23.95% by weight of coconut fatty acid methyl ester (an approximately 50:50 mix of methyl palmitate and methyl oleate) are mixed and stirred until a clear solution forms. This solution is then mixed with 75 to 95% by weight of 40–60 mesh corncob grits and the whole stirred until all of the solution is absorbed.

The above-referred-to tall oil fatty acid has the following typical composition:

| Components | % by weight |
|---|---|
| Composition: | |
| Moisture, | 0.1 |
| Ash, | 0.001 |
| Rosin Acids, | 0.5 |
| Unsaponifiables, | 0.7 |
| Fatty Acids Total, | 98.8 |
| Fatty Acid Composition: | |
| Linoleic, Non-Conjugated, | 38.0 |
| Linoleic, Conjugated, | 7.0 |
| Oleic, | 50.0 |
| Stearic Acid, | 2.0 |
| Other Fatty Acids, | 3.0 |

| Characteristics | Value |
|---|---|
| Color, Gardner, 1963 | 3— |
| Acid Value | 198.0 |
| Saponification Value | 200.0 |
| Iodine Value (Wijs) | 130.0 |
| Specific Gravity, 25°/25° C. | 0.897 |
| Viscosity, SUS, 3.8° C. | 95.0 |
| Flash Point, Open Cup, °C. | 204.0 |
| Fire Point, Open Cup, °C. | 227.0 |

The invention is further illustrated by the following non-limiting Examples.

EXAMPLE 1

Oleic acid salt of 1-(4'-amino-3',5'-dichlorophenyl)-2-t-butylaminoethanol

A solution of oleic acid (5.65 grams; 0.02 mol) in methylene chloride (5 ml) is added to a warmed up slurry of 1-(4'-amino-3',5'-dichlorophenyl)-2-t-butylaminoethanol (5.54 grams; 0.02 mol) in methylene chloride (30 ml). The mixture is stirred for a few minutes. The resultant solution is then filtered and evaporated to dryness to afford the title product, a slightly sticky solid, having a melting point from 54°–56° C. The product is soluble in ether, hexane, methanol, chloroform and ethylene dichloride.

By the above method, a number of salts of the title compound are prepared. These salts and data pertaining to same are compiled in Table I below.

TABLE I

Preparation of oil soluble salts of 1-(4'-amino-3,5'-dichlorophenyl)-2-t-butylaminoethanol ("base") with various acids

| No | Acid | Molar ratio of acid:base | Solvent(s) used | Salt forming reaction Temperature (C.°) | Melting point of salt (C.°) |
|---|---|---|---|---|---|
| 1 | $CH_3(CH_2)_7CH=CH(CH_2)_7COOH$<br>oleic acid | 1:1 | methylene chloride | slightly above ambient | 54–56 |
| 2 | $CH_3(CH_2)_3-(CH_2-CH=CH)_2-(CH_2)_7-COOH$<br>linoleic acid | 1:1 | methanol | ambient | waxy solid |
| 3 | $CH_3-(CH_2-CH=CH)_3-(CH_2)_7-COOH$<br>linolenic acid | 1:1 | methanol | ambient | pale amber oil |
| 4 | 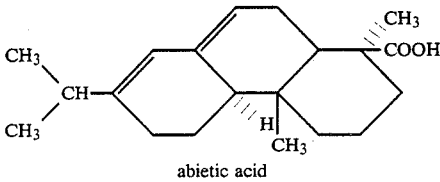abietic acid | 1:1 | methanol | above ambient | 85–95 |

EXAMPLE 2

Evaluation of the solubility of various salts of 1-(4'-amino-3',5'-dichlorophenyl)-2-t-butylaminoethanol in pharmaceutically acceptable solvents

Method

A predetermined amount of the appropriate salt is mixed with sufficient solvent to provide a mixture containing 10% W/W of 1-(4'-amino-3',5'-dichlorophenyl)-2-t-butylaminoethanol. The mixture is then agitated for 30 minutes at room temperature by ultrasonic waves. The mixtures are then visually examined.

By the above method, the solubility of the various salts is determined in propylene glycol, mineral oil and coconut fatty acid methyl ester (an approximately 50:50 mixture of methyl palmitate and methyl oleate). The results are presented in Table II below.

TABLE II

Solubility of acid salts of 1-(aminodihalophenyl)-2-aminoethanols

| No | Salt | Propylene glycol | Coconut fatty acid methyl ester | Mineral oil | Soybean oil | Corn oil |
|---|---|---|---|---|---|---|
| 1 | Acetate | I | I | I | I | I |
| 2 | Butyrate | S | I | I | I | I |
| 3 | Maleate | I | I | I | I | I |
| 4 | Citrate | S | I | I | I | I |
| 5 | Tartrate | I | I | I | I | I |
| 6 | Caproate | S | I | I | I | I |
| 7 | Laurate | S | I | I | I | I |
| 8 | Stearate | I | I | I | I | I |
| 9 | Lauryl Sulfate | S | I | I | I | I |
| 10 | Lactate | S | I | I | I | I |
| 11 | Naphthlenesulfonate | I | I | I | I | I |
| 12 | Oleate | S | S | I | I | I |
| 13 | Linoleate | PS | S | I | PS | PS |
| 14 | Linolenate | PS | PS | I | I | I |
| 15 | Abietate | S | S | I | S | S |

I = Apparent Total Insolubility
PS = Partially Soluble
S = Complete Soluble at 10% w/w It can be seen from the above Table that the abietate and the linoleate salts of the title compound show acceptable solubility in a number of solvents. Propylene glycol is the solvent in which most of the salts tested have acceptable solubility.

EXAMPLE 3

Antilipogenic evaluation of test compounds—Mouse Study

CIF female mice, 55 days old, are weighed in groups of 10 and allotted to cages to minimize weight variation among cages. The cages are kept in air-conditioned rooms (22° C. to 24° C.) with diurnal illumination (14 hours of light followed by 10 hours of darkness). The basal diet used in these studies is Purina Laboratory Chow (see description below), which is supplied ad libitum. The following is a description of the diet to which the antilipogenic compounds were added.

| DIET Guaranteed Analysis | |
|---|---|
| Crude protein not less than | 23.0% |
| Crude fat not less than | 4.5% |
| Crude fiber not more than | 6.0% |
| Ash not more than | 9.0% |

Ingredients

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. Water is also allowed ad libitum.

Treatments are randomly assigned to cages. Each of the treatments is tested in 3 replicate groups, i.e., in 3 cages of 10 mice each. There are 10 cages of 10 control mice each. Drugs are mixed in the diet at the dosage level indicated. Feed spilled is collected during the test period. At the end of the 12-day test period, the collected feed is weighed and the mean feed consumption per cage of 10 mice is determined for each treatment. The mice are weighed as a group of 10 and the weight gain determined. The mice are sacrificed by cervical dislocation. The right uterine fat pad of each mouse is removed. The fat pads for each cage of 10 mice are weighed as a unit.

Data obtained are reported in Table III below, wherein it can be clearly seen that the compounds of the invention increase the weight of the animals and reduce the uterine fat pad weights. Reduction in uterine fat pad weights of animals is generally indicative of a reduction of total body fat of the treated animals.

Additionally, it can be seen that at equivalent rates of active ingredient the acid salts of the invention tend to give more consistant and in general, greater weight gains than the free base.

EXAMPLE 4

Preparation of an oil concentrate of a novel salt of the invention and the concomitant preparation of a feed premix therefrom A mixture of 1-(4'-amino-3',5'-dichlorophenyl)-2-t-butylaminoethanol (7% by weight), oleic acid (7% by weight), sorbitan monooleate (20% by weight), and mineral oil (66% by weight) are mixed and stirred until a clear solution forms [in situ preparation of the oleate salt] containing 7% by weight of the desired active ingredient.

A mixture of the above oil concentrate (6% by weight) and 40–60 mesh corncob grits (94% by weight) is blended and agitated until all of the liquid is absorbed, affording a feed premix containing 0.4% by weight (5% excess over theory added) of 1-(4'-amino-3',5'-dichlorophenyl)-2-t-butylaminoethanol oleate.

EXAMPLE 5

Preparation of a feed premix containing 1-(4'-amino-3',5'-dichlorophenyl-2-t-butylaminoethanol salt A mixture of 1-(4'-amino-3',5'-dichlorophenyl)-2-t-butylaminoethanol (0.10% by weight), tall oil fatty acid (0.11% by weight) and coconut oil fatty acid methyl ester (4.79% by weight) is stirred with gentle heating until a clear solution forms. This solution is then mixed with 40–60 mesh corncob grits (95%) and blended until all of the liquid is absorbed to afford a feed premix containing 0.1% by weight of the salt of the title compound.

What is claimed is:

1. A method for increasing the weight gain of warm-blooded animals and improving the lean meat to fat ratio of said animal comprising: incorporating as an active ingredient in the diet of said animals about 1 to 250 ppm of the salt 1-(4'-amino-3',5'-dichlorophenyl)-2-t-butylaminoethanol oleate.

* * * * *

TABLE III

Evaluation of the antilipogenic effect of a salt of the invention using mice as test animal

| Compound | Level in diet (ppm) | No of mice per treatment | Average weight per group Initial (g) | Average weight per group Final (g) | Gain per group (g) | % change (±) from control | Fat pad per group weight (g) | Fat pad per group % change (±) from control |
|---|---|---|---|---|---|---|---|---|
| Control | 0 | 100 | 236.2 | 251.0 | 14.8 | — | 1.986 | — |
| 1-(4'-Amino- | 3 | 30 | 235.5 | 259.4 | 23.9 | +61.5 | 1.871 | −5.8 |
| 3',5'-dichloro- | 6 | 30 | 241.7 | 266.2 | 25.2 | +70.3 | 1.846 | −7.0 |
| phenyl)-t- | 12 | 30 | 234.1 | 258.2 | 24.2 | +63.5 | 1.656 | −16.6 |
| butylamino- | 25 | 30 | 238.1 | 262.3 | 24.2 | +64.2 | 1.871 | −5.8 |
| ethanol | 50 | 30 | 233.5 | 257.0 | 23.5 | +58.8 | 1.457 | −26.6 |
|  | 100 | 30 | 238.5 | 257.9 | 19.4 | +31.8 | 1.345 | −32.3 |
|  | 200 | 30 | 241.5 | 256.5 | 15.1 | +2.7 | 1.209 | −39.1 |
| Oleic acid | 3 | 30 | 235.9 | 261.0 | 25.1 | +69.6 | 2.057 | +3.6 |
| salt of | 6 | 30 | 236.3 | 260.8 | 24.5 | +65.5 | 2.188 | +10.2 |
| 1-(4'-amino- | 12 | 30 | 234.5 | 259.1 | 25.2 | +70.9 | 1.960 | −1.3 |
| 3',5'-dichloro- | 25 | 30 | 237.1 | 262.7 | 25.6 | +73.0 | 1.533 | −22.8 |
| phenyl)-t- | 50 | 30 | 233.3 | 256.3 | 23.0 | +54.7 | 1.559 | −21.5 |
| butylamino- | 100 | 30 | 237.1 | 258.9 | 21.8 | +47.3 | 1.231 | −38.0 |
| ethanol | 200 | 30 | 236.2 | 257.5 | 21.3 | +43.9 | 1.085 | −45.4 |